(12) United States Patent
Sedghi

(10) Patent No.: US 12,016,791 B2
(45) Date of Patent: Jun. 25, 2024

(54) INTRAGASTRIC MAGNETIC DEVICE AND DELIVERY SYSTEM

(71) Applicant: Shahriar Sedghi, Macon, GA (US)

(72) Inventor: Shahriar Sedghi, Macon, GA (US)

(73) Assignee: APPETEC INC, Macon, GA (US)

( * ) Notice: Subject to any disclaimer, the term of this patent is extended or adjusted under 35 U.S.C. 154(b) by 162 days.

(21) Appl. No.: 17/491,450

(22) Filed: Sep. 30, 2021

(65) Prior Publication Data

US 2023/0100738 A1 Mar. 30, 2023

(51) Int. Cl.
*A61F 5/00* (2006.01)

(52) U.S. Cl.
CPC ............ *A61F 5/0036* (2013.01); *A61F 5/003* (2013.01); *A61F 2005/0016* (2013.01)

(58) Field of Classification Search
CPC .. A61M 2210/1053; A61M 2025/1054; A61M 2025/1059; A61M 2025/1063; A61M 2025/1065; A61M 2025/1077; A61F 5/003; A61F 5/0033; A61F 5/0036; A61F 5/005; A61F 5/004; A61F 5/0043; A61F 5/0046; A61F 5/0069; A61F 5/0073; A61F 5/0076; A61F 5/0079; A61F 5/0083; A61F 5/0053; A61F 5/0063; A61F 5/0066; A61F 5/0056; A61F 5/0059; A61F 5/0089; A61F 5/0003; A61F 5/00; A61F 2005/0016; A61F 2005/002; A61F 2005/0023; A61F 5/0013

See application file for complete search history.

(56) References Cited

U.S. PATENT DOCUMENTS

| | | | | |
|---|---|---|---|---|
| 2017/0157361 A1* | 6/2017 | Barrish | ............ | A61B 17/00234 |
| 2017/0367863 A1* | 12/2017 | McCarthy | ............. | A61F 5/0036 |
| 2018/0161187 A1* | 6/2018 | Sedghi | .................. | A61M 31/00 |
| 2022/0346996 A1* | 11/2022 | Favreau | .................... | A61F 2/04 |

FOREIGN PATENT DOCUMENTS

| EP | 2732799 A1 * | 5/2014 | ............... A61F 2/04 |
|---|---|---|---|
| WO | WO-2018169805 A1 * | 9/2018 | |

* cited by examiner

*Primary Examiner* — Brooke Labranche
*Assistant Examiner* — Nasheha Baset
(74) *Attorney, Agent, or Firm* — Select IP Law Corporation; Ashkon Cyrus

(57) ABSTRACT

The present disclosure provides an intragastric implant capable of inducing the feeling of satiety from inside the stomach, together with a delivery device for delivering said implant. The system and method provides greater access to minimally invasive weight loss procedures for patients who are only overweight or obese, reducing the risks associated with more invasive procedures.

7 Claims, 6 Drawing Sheets

FIG. 4A
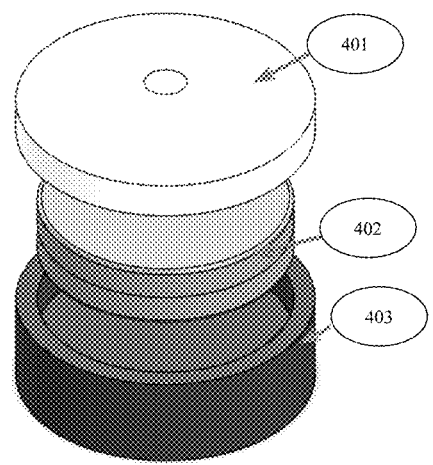
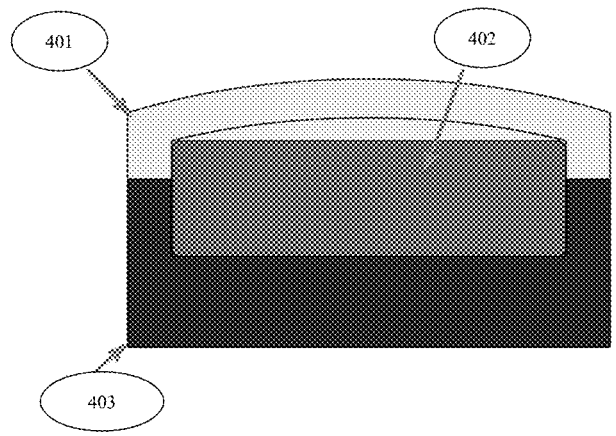
FIG 4B

INTRAGASTRIC MAGNETIC DEVICE AND DELIVERY SYSTEM

TECHNICAL FIELD

The present disclosure relates to medical implants and delivery devices.

BACKGROUND OF THE DISCLOSURE

Obesity is a major medical problem affecting millions of people. It is generally considered that obesity is a food addiction problem.

Obese patients currently undergo several types of invasive surgery to either staple or tie off portions of the stomach, small intestine, and/or bypass portions of the same. The goal is to reduce the amount of food desired by the patient. Current methods for achieving these results include laparoscopic banding, surgical bypass, and gastric stapling. These methods often necessitate incisions and general anesthesia, and may cause long- or short term complications.

Less invasive endoscopic procedures are also used to assist weight loss, and have primarily focused on placement of a balloon or other space-occupying device in the patient's stomach to provide a continual feeling of fullness and consequential reduction in food intake, often in conjunction with behavioral modification programs.

To accomplish these procedures, an endoscope is generally utilized to guide the space-occupying device through the patient's mouth, down the esophagus, and into the stomach before relinquishing control of the device for some 4-12 months, and endoscopically retrieving it thereafter. Additionally, air leakiness especially is a major problem with current balloons. It is typically the case that the smaller the balloon, the higher the pressure with more leakiness.

There exists a need in the art to address the problems described above.

SUMMARY OF THE DISCLOSURE

The present disclosure provides an intragastric implant capable of inducing the feeling of satiety from inside the stomach, together with a delivery device for delivering said implant.

In addition to patients who may otherwise be treated surgically as morbidly obese, the invention provides greater access to minimally invasive weight loss procedures for patients who are only moderately overweight or obese, reducing the risks associated with more invasive procedures.

Although specific advantages have been enumerated above, various embodiments may include some, none, or all of the enumerated advantages. Additionally, other technical advantages may become readily apparent to one of ordinary skill in the art after review of the following figures and description.

BRIEF DESCRIPTION OF THE DRAWINGS

For a more complete understanding of the present disclosure and its advantages, reference is now made to the following description taken in conjunction with the accompanying drawings, in which like reference numerals represent like parts.

FIGS. 4A and 4B show views of a poron/plastic covered magnet for impact absorption.

DETAILED DESCRIPTION OF THE DISCLOSURE

Figure 1:
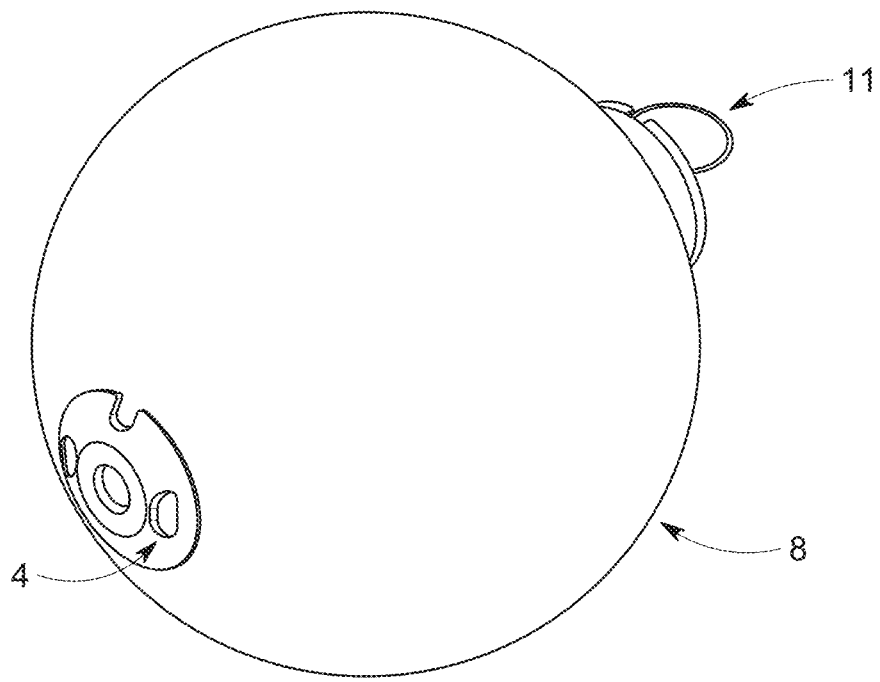
FIG. 1 is a perspective view of the inner core of a magnetic intragastric device.

It should be understood at the outset that, although exemplary embodiments are illustrated in the figures and described below, the principles of the present disclosure may be implemented using other techniques. The present disclosure should in no way be explicitly limited to the exemplary implementations and techniques illustrated in the drawings and described below. Additionally, unless otherwise specifically noted, articles depicted in the drawings are not necessarily drawn to scale The present invention discloses intragastric medical devices which may be implanted within a patient's body without surgery. The intragastric device can be controlled remotely with external devices using the forces of magnetic attraction and repulsion.

With specific reference to the embodiments and figures in detail, it is stressed that the particulars presented are by way of example for purposes of illustrative discussion of embodiments of the present invention only and are presented to provide what is believed to be the most readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

An intragastric device is presented in FIG. 1, which shows an outer view of a tubular intragastric device in its default deployed state. The intragastric device has a balloon 8 with a suture wire 11 appearing on a distal side of the balloon and a valve cover 4 appearing on the distal side.

Figure 2A:
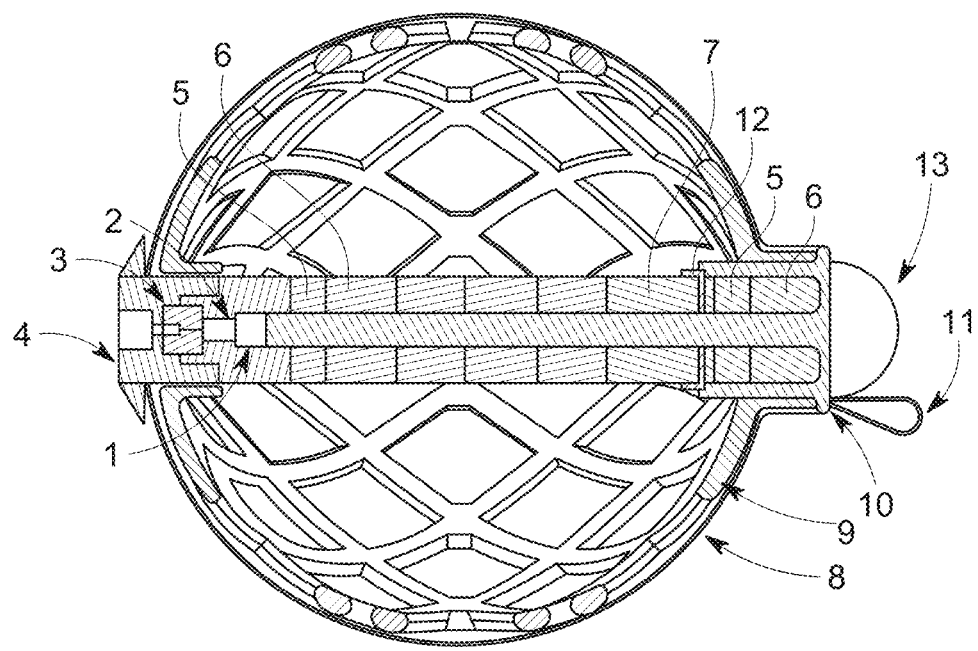
FIG. 2A is a cross-sectional view of a magnetic intragastric device.
Figure 2B:
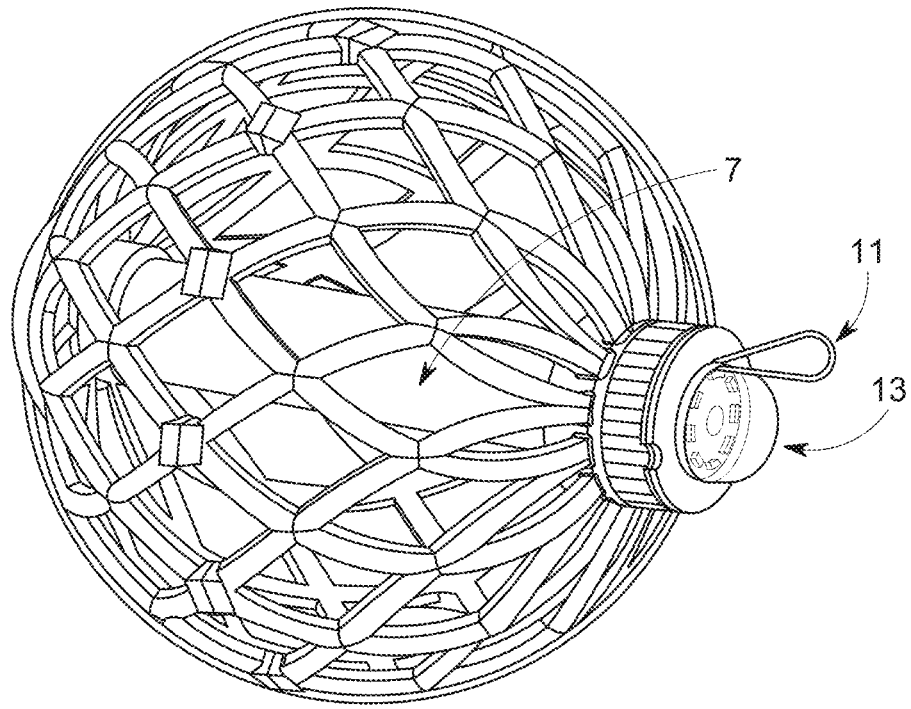
FIG. 2B is a perspective view of a magnetic intragastric device.

The intragastric device 100 is also presented in FIG. 2A, which shows a cross sectional view of a tubular intragastric device in its default deployed state. A pair of magnets 5 and 6 are located on the distal side, within a magnet enclosure cap 12. A core inner tube 1 goes through the middle of the device and attaches to the valve housing 2, with a septum 3 appearing at the end of the valve housing. Valve cover 4 is connected to the valve housing 2. A single piece stent 9 is placed within the balloon 8. An outer core tube 7 appears outside the inner core tube 1. Also provided is a suture loop 11 and appendage 13. A snare collar 10 is provided at the distal end of the intragrastric device. FIG. 2 B shows a perspective view of an intragastric device.

According to an embodiment, appendage 13 further comprises a sensor. The optional sensor can monitor drug delivery, according to this embodiment. In alternative embodiments, the sensor could monitor acidity, motility, disease, and other physiologic functions such as a pressure sensor. Thus, it can be appreciated that the function and usage of the balloon can be monitored from outside. By having pressure sensors, the patient or an AI system could identify which area of the stomach at which pressure. gives the best desired outcome.

In a further embodiment, the sensor could monitor movement of the device According to an embodiment, the sensor comprises an accelerometer. According to another embodiment, the sensor further comprises a hardware-based gyroscope. The sensor could further comprise a camera. The camera can be used long term to monitor healing of an ulcer or response to treatment of cancer or for chronic GI bleed, as examples. The sensor is operable to monitor linear acceleration, significant motion, rotation vector, step counter, and step detector sensors, via methods that are either hardware-based or software-based, as understood with such sensors currently available.

The sensor can be configured to measure and store data including optical data and be retrieved when the balloon is moved endoscopically and/or use a remote monitor to deliver data.

In an alternative embodiment, appendage 13 further comprises a drug delivery system, along with a remote monitoring system which is responsible for administering a drug contained in the appendage 13.

According to an embodiment, the stent 9 comprises a mesh-like pattern.

It can be appreciated that in a collapsed state, the stent can be placed within the delivery device.

In an alternative embodiment, a single magnet may be used instead of multiple magnets. The magnets comprise neodymium magnetics according to an embodiment.

Figure 3A:
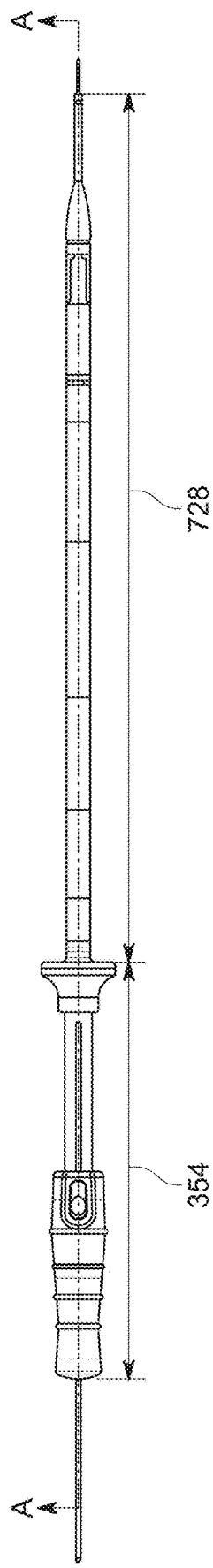
FIG. 3A and FIG. 3B are perspective views of a delivery device for the intragastric device.
Figure 3B:
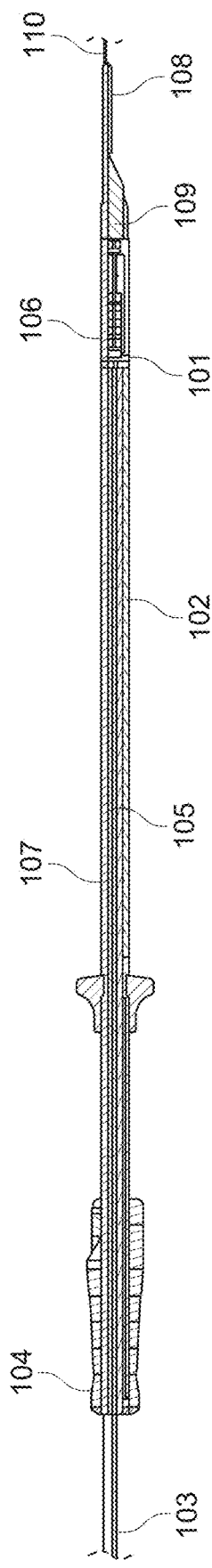

A first embodiment of a delivery device is presented in FIGS. 3A and 3B. An intragastric device in collapsed state is placed within a device deployment holder. A guide wire 110 runs though the dilator tip and is intended to guide the intragastric device 101 through an esophagus. The guide wire is surrounded by a guide wire tube 107. Also included is an inflation tube assembly 103, a sheath 102, deployment handle assembly 104, device deployment holder 106, a dilator tip 108, inner sheath 109, and a silicone support tube 105.

The collapsed state disclosed in FIGS. 3A and 3B is used during delivery of the intragastric device into the stomach of the patient. The spring loaded stent expands the intragastric device upon insertion into a patient's stomach, such that the stent is expanded into a balloon like structure. That is, once the device exits the esophagus and enters the stomach, the device's resilient and flexible structure reverts to its natural expanded state, in this case a balloon shape.

In one embodiment, the system is sealed so upon deployment it can't self-expand. Instead, an inflation tube is provided to expand the system. Once the inflation catheter tip is opened, the implant can self-expand or be aided in expansion by injection of air.

In a further novel embodiment, there is a small magnet on the other side of the tube that is attracted to the main set of magnets. It can be appreciated that this helps the frame to expand and acquire its structure. This feature is important as the delivery device is held inside a delivery tube for a period of time, thus it many take a while for the frame to fully acquire an expanded shape without this extra small magnet.

In a further embodiment, a silicone membrane is outside the frame and loose. Hence the device is a zero/low pressure system that does not leak air through silicone or through the valve. The primary function of the silicone membrane outside of the frame is to prevent food getting stuck in the frame.

In a further embodiment, an external device containing one or more magnets are provided to operate the system, together with safety features.

FIGS. 4A and 4B show a poron/plastic covered magnet for impact absorption. A magnet 402 is placed within a poron foam container 403 with a plastic upper case 401.

Figure 5A:
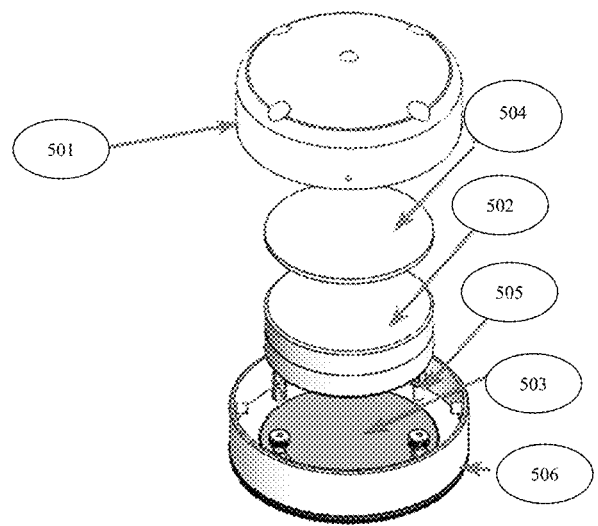
FIGS. 5A and 5B show views a magnet within a plunger system.
Figure 5B:
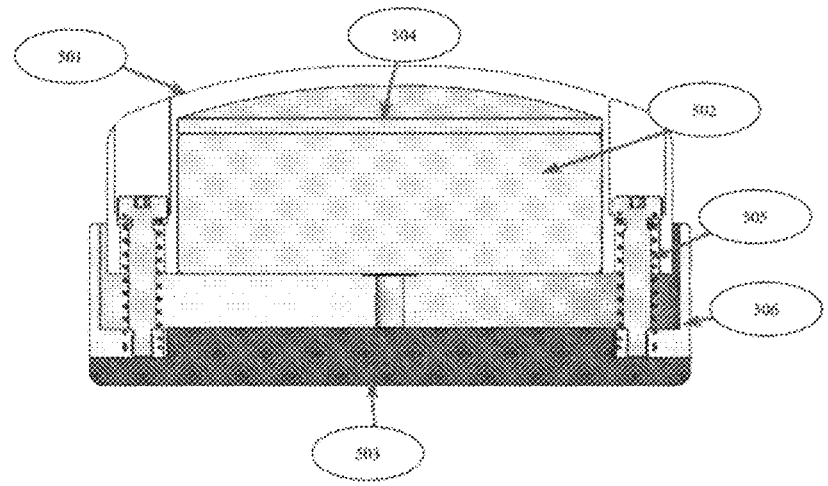

FIGS. 5A and 5B show a magnet 502 within a plunger system that has to be pushed down to be "activated". When released by hand, the springs 505 push it back up creating space and sharply dropping magnetic force. The magnet 502 is placed within a poron foam container 503 with a plastic upper case 501 and shield 504 within lower case 506.

Figure 6:
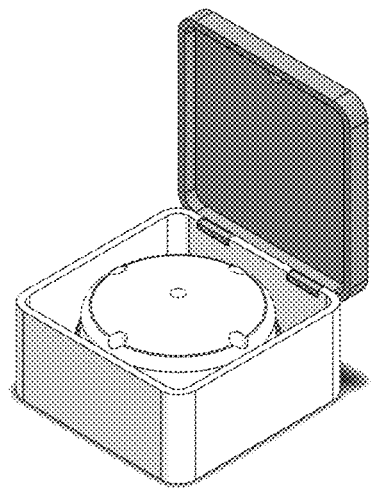
FIG. 6 shows a view of a storage box with sensor/alarm for remote monitoring.

FIG. 6 shows a storage box with sensor/alarm for remote monitoring and also to alert the user that the external magnet is not properly stored. In a further embodiment, RF sensors are added on the external magnet too to show how often they are being used.

Modifications, additions, or omissions may be made to the systems, apparatuses, and/or methods described herein without departing from the scope of the disclosure. For example, various components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A balloon stent implant, comprising:
   a balloon with a proximate end and a distal end;
   a stent within the balloon;
   a core inner tube going through a middle of the balloon from the proximate end to the distal end;
   one or more magnets at the distal end;
   a core outer tube outside the core inner tube;
   a suture loop; and
   a magnet on the proximate end of the tube configured to expand the deflated structure to its inflated shape by magnetic attraction to the one or more magnets at the distal end.

2. The balloon stent of claim 1, wherein the one or more magnets at the distal end further comprises a neodymium magnet.

3. The balloon stent of claim 2, further comprising a sensor at the proximate end.

4. The balloon stent of claim 3, wherein the sensor further comprises an accelerometer.

5. The balloon stent of claim 3, wherein the sensor further comprises a gyroscope.

6. The balloon stent of claim 3, wherein the sensor further comprises a camera.

7. A deployment catheter, comprising:
   the balloon stent implant of claim 1;
   a sheath
   an inflation tube assembly;
   a deployment handle assembly;
   a silicone support tube;
   a device deployment holder;
   a guide wire tube;
   a dilator tip;

an inner sheath; and a guide wire going through the guide wire tube.

* * * * *